(12) United States Patent
Zhang et al.

(10) Patent No.: US 10,695,056 B2
(45) Date of Patent: Jun. 30, 2020

(54) ELECTRIC SURGICAL STAPLER

(71) Applicant: SUZHOU INTOCARE MEDICAL TECHNOLOGY CO., LTD., Suzhou (CN)

(72) Inventors: Hui Zhang, Suzhou (CN); Yunfeng Du, Suzhou (CN); Dianchen Liu, Suzhou (CN); Aiyu Huang, Suzhou (CN)

(73) Assignee: SUZHOU INTOCARE MEDICAL TECHNOLOGY CO., LTD., Suzhou (CN)

( * ) Notice: Subject to any disclaimer, the term of this patent is extended or adjusted under 35 U.S.C. 154(b) by 343 days.

(21) Appl. No.: 15/567,161

(22) PCT Filed: Jul. 29, 2016

(86) PCT No.: PCT/CN2016/092394
§ 371 (c)(1),
(2) Date: Oct. 17, 2017

(87) PCT Pub. No.: WO2017/107489
PCT Pub. Date: Jun. 29, 2017

(65) Prior Publication Data
US 2018/0280026 A1    Oct. 4, 2018

(30) Foreign Application Priority Data
Dec. 22, 2015 (CN) .......................... 2015 1 0975918

(51) Int. Cl.
*A61B 17/072* (2006.01)
*A61B 17/115* (2006.01)
(Continued)

(52) U.S. Cl.
CPC .... *A61B 17/07207* (2013.01); *A61B 17/1155* (2013.01); *A61B 17/1114* (2013.01);
(Continued)

(58) Field of Classification Search
CPC .................. A61B 17/07207; A61B 17/1155
(Continued)

(56) References Cited

U.S. PATENT DOCUMENTS

| 2008/0185419 A1* | 8/2008 | Smith | A61B 90/98 |
|---|---|---|---|
| | | | 227/179.1 |
| 2010/0096431 A1* | 4/2010 | Smith | A61B 17/00 |
| | | | 227/175.2 |

(Continued)

FOREIGN PATENT DOCUMENTS

| CN | 102247182 A | 11/2011 |
|---|---|---|
| CN | 202044308 U | 11/2011 |

(Continued)

OTHER PUBLICATIONS

International Search Report for International Application No. PCT/CN2016/092394 dated Oct. 25, 2016, 6 pages.
(Continued)

*Primary Examiner* — Nathaniel C Chukwurah
(74) *Attorney, Agent, or Firm* — Seyfarth Shaw LLP

(57) ABSTRACT

An electric surgical stapler and a method for controlling closing and firing of the electric surgical stapler are disclosed. The electric surgical stapler includes: a driving motor, having an output shaft; a working head, including an anvil, a cartridge, a closing mechanism, a firing mechanism, a closing limit switch, and a firing safety switch, wherein the closing limit switch is configured to detect a closing stroke of the closing mechanism, the firing safety switch has a closing position and a firing position, the firing safety switch is configured to allow the output shaft to transmit power to the closing mechanism when the firing safety switch is at the closing position, and the firing safety switch is configured to allow the output shaft to transmit power to the firing mechanism when the firing safety switch is at the firing position; and a control unit, including: a working head
(Continued)

identifying module; a motor control module; a closing and firing control module, configured to receive information transmitted from the closing limit switch and the firing safety switch; a closing switch; and an opening switch. The control unit is provided with a plurality of modules, and is able to communicate with the working head in real time, to avoid abnormal or fault operations during surgery, and to improve security in use.

10 Claims, 4 Drawing Sheets

(51) Int. Cl.
*A61B 90/00* (2016.01)
*A61B 90/98* (2016.01)
*A61B 17/00* (2006.01)
*A61B 17/11* (2006.01)

(52) U.S. Cl.
CPC ..... *A61B 90/98* (2016.02); *A61B 2017/00017* (2013.01); *A61B 2017/00022* (2013.01); *A61B 2017/00039* (2013.01); *A61B 2017/00119* (2013.01); *A61B 2017/00128* (2013.01); *A61B 2017/00221* (2013.01); *A61B 2017/00398* (2013.01); *A61B 2017/00464* (2013.01); *A61B 2017/00734* (2013.01); *A61B 2017/07257* (2013.01); *A61B 2017/07271* (2013.01); *A61B 2090/032* (2016.02); *A61B 2090/065* (2016.02); *A61B 2090/0807* (2016.02)

(58) Field of Classification Search
USPC ...................................................... 227/176.1
See application file for complete search history.

(56) References Cited

U.S. PATENT DOCUMENTS

| | | |
|---|---|---|
| 2014/0012289 A1 | 1/2014 | Snow et al. |
| 2015/0122870 A1 | 5/2015 | Zemlok et al. |
| 2015/0223818 A1 | 8/2015 | Racenet et al. |

FOREIGN PATENT DOCUMENTS

| | | |
|---|---|---|
| CN | 103110439 A | 5/2013 |
| CN | 103405254 A | 11/2013 |
| CN | 103405257 A | 11/2013 |
| CN | 105411642 A | 3/2016 |
| EP | 2792306 A2 | 10/2014 |

OTHER PUBLICATIONS

Chinese Office Action for Chinese Application No. 201510975918.2 dated Feb. 17, 2017, 4 pages.
Chinese Office Action for Chinese Application No. 201510975918.2 dated Jul. 10, 2017, 7 pages.
Chinese Search Report for Chinese Application No. 201510975918.2 dated Dec. 22, 2015, 1 page.
Written Opinion for International Application No. PCT/CN2016/092394 dated Oct. 25, 2016, 5 pages.
European Search Report for Application No. 16877301.8 dated Aug. 26, 2019, 8 pages.

* cited by examiner

ELECTRIC SURGICAL STAPLER

CROSS REFERENCE TO RELATED APPLICATIONS

This is a National Stage application of PCT/CN2016/092394, filed Jul. 29, 2016, and claims priority to Chinese Patent Application Serial No. CN 201510975918.2, filed Dec. 22, 2015, the disclosures of which are incorporated herein by reference.

TECHNICAL FIELD

The present disclosure relates to the technical field of medical equipment, and more particularly, to an electric surgical stapler.

BACKGROUND

Manual surgical staplers play a dominant role in surgical anastomosis at present, but electric surgical staplers can eliminate the influence of manual operation on the precision of staple formation, while achieving objectives of environmental protection and cost reduction by reusing the electric handle.

Whether the electric surgical stapler is comfortable for use and has abilities of precise closing, staple formation and cutting depends on good communication between the handle and the working head. The electric surgical stapler is required to ensure that fault operations, tissue necrosis caused by the excessive closing of the electric surgical stapler to squeeze the tissue, and deformation of the staple caused by the excessive firing of the electric surgical stapler are avoided, to improve the efficiency of the surgery and to accelerate the postoperative recovery.

SUMMARY

Based on the above, an objective of the present disclosure is to provide an electric surgical stapler to avoid abnormal or fault operations during surgery, and to improve security in use. Another objective of the present disclosure is to provide a method for controlling closing and firing of the electric surgical stapler.

According to an aspect of the present disclosure, an electric surgical stapler is provided, including:

a driving motor, having an output shaft;

a working head, including an anvil, a cartridge, a closing mechanism, a firing mechanism, a closing limit switch, and a firing safety switch, wherein the closing limit switch is configured to detect whether a closing stroke of the closing mechanism comes within a predetermined range, the firing safety switch has a closing position and a firing position, the firing safety switch is configured to allow the output shaft to transmit power to the closing mechanism when the firing safety switch is at the closing position, and the firing safety switch is configured to allow the output shaft to transmit power to the firing mechanism when the firing safety switch is at the firing position; and a control unit, including:

a working head identifying module, configured to acquire identification information of the working head;

a motor control module, configured to control starting and stopping of the driving motor;

a closing and firing control module, configured to receive closing stroke information transmitted from the closing limit switch, and receive position information transmitted from the firing safety switch;

a closing switch, configured to transmit a closing instruction to the motor control module; and an opening switch, configured to transmit an opening instruction to the motor control module.

In the electric surgical stapler according to the above aspect, the control unit is provided a plurality of modules, and is able to communicate with the working head in real time, so that a next action is implemented only when the feedback is normal to avoid abnormal or fault operations during surgery, and to improve security in use.

In one embodiment, the electric surgical stapler further includes: an adjustment screw for controlling rotation of the output shaft, configured to adjust the output shaft manually to control the closing mechanism or firing mechanism.

In one embodiment, the electric surgical stapler further includes: a pressure sensor, configured to detect a closing pressure value of the anvil and the cartridge during a closing process, and transmit the closing pressure value to the control unit.

In one embodiment, the electric surgical stapler further includes: a firing limit switch, configured to detect whether a firing stroke of the firing mechanism comes within a predetermined range, and transmit a detection result to the control unit.

In one embodiment, the electric surgical stapler further includes a battery pack, and the control unit further includes a battery detection module configured to detect a battery level of the battery pack.

In one embodiment, the control unit further includes a battery detection module configured to detect a battery level of the battery pack.

In one embodiment, the control unit further includes a data recoding and storing module configured to record each closing stroke.

According to another aspect of the present disclosure, a method for controlling closing and firing of the above electric surgical stapler is provided, including:

acquiring the identification information of the working head;

acquiring state information of the firing safety switch at the closing position or firing position, and controlling the anvil and the cartridge of the working head to open a corresponding distance from a closing state, based on the identification information of the working head, when detecting the firing safety switch is at the closing position and the closing limit switch is triggered;

detecting whether the closing switch is triggered and the firing safety switch is at the closing position, and is so, starting the driving motor and controlling operation of the closing mechanism to gradually close the anvil and the cartridge, and stopping the driving motor when the closing limit switch is triggered, otherwise switching the firing safety switch to the closing position, and continuing to detect whether the closing switch is triggered; and detecting whether the closing switch is triggered, the firing safety switch is at the firing position, and the closing limit switch is at a triggering position, and if so, activating the driving motor to drive the firing mechanism to operate, otherwise, switching the firing safety switch to the firing position, and continuing to detect whether the closing switch is triggered.

In the method according to the above aspect, during the closing and firing, each operation is performed when the feedback of the last operation is consistent with the predetermined standard, to ensure any abnormal or fault operation will not happen during the choice and usage of the working head, to reduce the influence of manual operation on the device, to improve the security of the usage of the device.

In one embodiment, the method further includes adjusting the closing mechanism manually when the closing limit switch is triggered and the driving motor is stopped, and switching the firing safety switch from the closing position to the firing position after the manual adjustment.

In one embodiment, the electric surgical stapler further includes a pressure sensor configured to detect the closing pressure value of the anvil and the cartridge during a closing process, and transmit the closing pressure value to the control unit; and the control unit is configured to transmit an instruction of controlling the driving motor to drive movement of the firing mechanism, when the closing limit switch is triggered and the pressure value transmitted by the pressure sensor meets a preset standard.

In one embodiment, the electric surgical stapler further includes a firing limit switch configured to detect whether a firing stroke of the firing mechanism comes within a predetermined range, and the driving motor is adapted to stop when the firing limit switch is triggered.

In one embodiment, the method further includes switching the firing safety switch to the closing position and making the driving motor rotate inversely to reset the closing mechanism, when the firing limit switch is triggered and the driving motor is stopped.

In one embodiment, acquiring the identification information of the working head includes: verifying the validity of the identification of the working head; and identify the type of the working head.

DETAILED DESCRIPTION

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

The preferred embodiments of the electric surgical stapler will be described taken in conjunction with the accompanying drawings.

Example One

Figure 1:
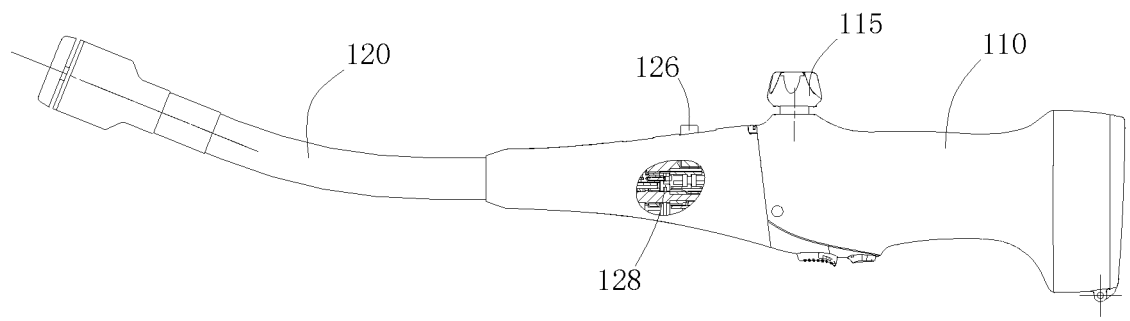
FIG. 1 is a schematic diagram illustrating an electric surgical stapler according to Example One of the present disclosure.

With reference to FIG. 1, an electric surgical stapler is provided, including a handle 110 and a replaceable working head 120.

Figure 2:
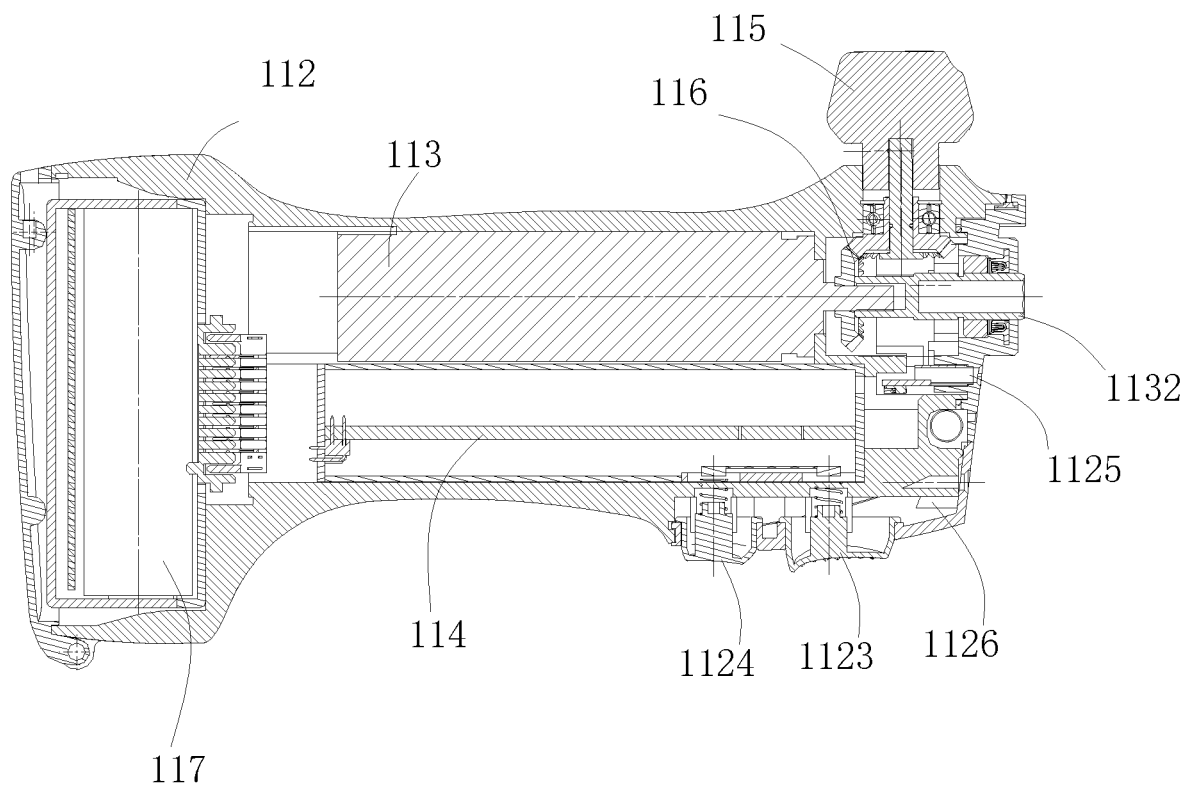
FIG. 2 is a schematic diagram illustrating a handle of the electric surgical stapler according to Example One of the present disclosure.

With reference to FIG. 2, the handle 110 is a driving device for driving the working head 120 to operate, including a hollow handle body 112, a driving motor 113 with an output shaft 1132, and a control unit 114, and the driving motor 113 and the control unit 114 are arranged inside the handle body 112.

The outer wall of the handle body 112 is provided with an adjustment knob 115. The adjustment knob 115 is connected to the output shaft 1132 through a bevel gear system 116. When the driving motor 113 stops, the user may turn the adjustment knob 115, and the bevel gear system 116 may drive the output shaft 1132 to rotate, to achieve manual adjustment. In this way, when there is a failure in the electric system, the manual mode may be enabled, in which the adjustment knob 115 may be used to open the jaw of the working head 120 or finish firing.

In this example, the working head 120 is a circular stapling head, including an anvil 121, cartridge 122, a closing mechanism, a firing mechanism, and a housing 125 housing the closing mechanism and the firing mechanism.

The closing mechanism includes a closing main shaft 1232 and a closing transmission mechanism. The rotation of the closing main shaft 1232 is driven by a driving motor 113. The closing transmission mechanism is connected to the anvil 121. When the closing main shaft 1232 rotates, a first linear motion component in the closing transmission mechanism drives the anvil 121 to move in a straight line. The first linear motion component includes a first sliding block 1234 and a first push rod 1235 driven by the first sliding block 1234. The first sliding block 1234 is connected to the closing main shaft 1232 in a helical transmission form, but the rotation of the first sliding block 1234 is limited. When the closing main shaft 1232 rotates, the first sliding block 1234 is able to move in a straight line, and drive the movement of the anvil 121 through the first push rod 1235.

The firing mechanism includes a firing main shaft 1242 and a firing transmission mechanism. The firing main shaft 1242 is driven by the driving motor 113 to rotate. The firing transmission mechanism is connected to a staple ejecting plate. When the firing main shaft 1242 rotates, a second linear motion component in the firing transmission mechanism causes the staple ejecting plate to perform firing actions. In this example, the second linear motion component is similar to the first linear motion component in the closing transmission mechanism. The second linear motion component includes a second sliding block 1244 and a second push rod 1245 driven by the second sliding block 1244. When the firing main shaft 1242 rotates, the second sliding block 1244 is able to move in a straight line, and drive the movement of the staple ejecting staple ejecting components in the cartridge 122 through the second push rod 1435.

The working head 120 further includes a firing safety switch 126 mounted on the housing 125. The firing safety switch 126 has a first operating position and a second operating position. The firing safety switch 126 allows the output shaft 1132 to transmit torque to the closing main shaft 1232 when the firing safety switch 126 is at the first operating position, and the first operating position is defined as a closing position. The firing safety switch 126 allows the output shaft 1132 to transmit torque to the firing main shaft 1242 when the firing safety switch 126 is at the second operating position, and the second operating position is defined as a firing position.

The firing safety switch 126 fits a switching transmission mechanism in the housing 125. The switching transmission mechanism includes an input shaft 1271, a switching shaft 1272, a switching driving lever 1273, a first switching ring 1274, a first guide block 1275, a second switching ring 1276 and a second guide block 1277 matching and connected to the output shaft 1132.

The input shaft 1271 transmits power to the switching shaft 1272 through a gear mechanism. The first guide block 1275 is fastened to the input shaft 1271, the first switching ring 1274 is able to drive the closing main shaft 1232 to rotate, and be driven by the switching driving lever 1273 to be engaged with or disengaged from the first guide block 1275. The second guide block 1277 is fastened to the firing main shaft 1242, the second switching ring 1276 is able to drive the firing main shaft 1242 to rotate, and be driven by the switching driving lever 1273 to be engaged with or disengaged from the second guide block 1277.

The firing safety switch 126 may be operated to drive the switching driving lever 1273, so that the first switching ring 1274 is engaged with the first guide block 1275 while the second switching ring 1276 is disengaged from the second guide block 1277, or the first switching ring 1274 is disengaged from the first guide block 1275 while the second switching ring 1276 is engaged with the second guide block 1277. In this way, the switching of the power transmission can be achieved by operating the firing safety switch 126.

The switching transmission mechanism may be implemented in other forms. For example, an intermediate shaft and a switching member matching and connected to the output shaft 1132 may be provided. The switching member may make an axially upward movement on the intermediate shaft, the switching member may connect the intermediate shaft to the closing main shaft 1232 at the first operating position, and the switching member may connect the intermediate shaft to the firing main shaft 1242 at the second operating position.

The handle 110 is only internally provided one driving motor 113 and one output shaft, and can switch power transmission by the firing safety switch 126. There may also be two driving motors 113, that is one driving motor is adapted to drive the closing main shaft 1232 alone, and the other driving motor is adapted to drive the firing main shaft alone.

Further, the firing safety switch 126 is mounted on the housing 125. The firing safety switch 126 may also be arranged on the handle body 112, that is, the switching mechanism for power transmission may be arranged within the handle 110.

Figure 3:
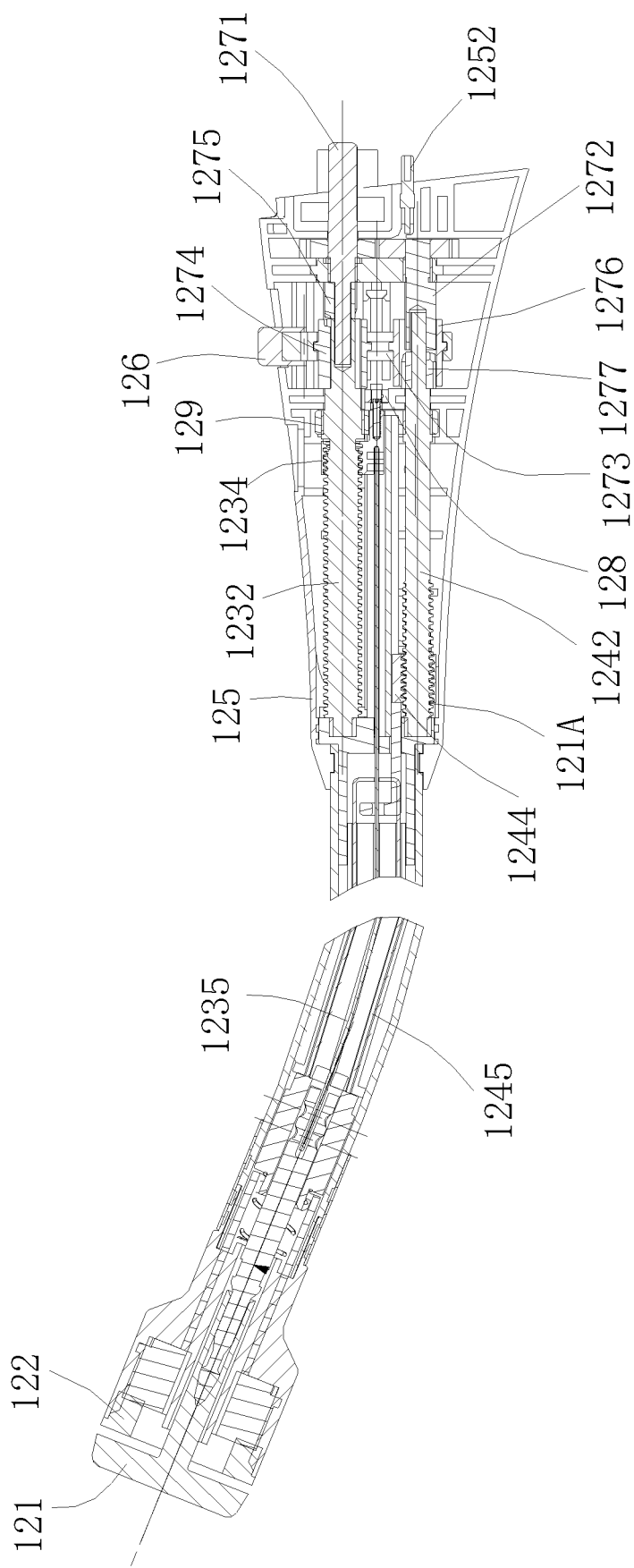
FIG. 3 is a schematic diagram illustrating a circular stapling head in the electric surgical stapler according to Example One of the present disclosure.

With reference to FIG. 3, the working head 120 also includes a closing limit switch 128 and a pressure sensor 129.

The closing limit switch 128 is configured to detect the closing stroke of the closing mechanism, and transmit information of the closing stroke to the control unit 114. The closing limit switch 128 may be an optoelectronic switch, a micro switch or a proximity switch.

The closing limit switch 128 is mounted on the housing 125. When the first linear motion component in the closing mechanism moves to a closing position within a preset range, the closing limit switch 128 may be triggered to transmit a signal to the control unit 114, indicating that the closing stroke comes within a preset range.

The pressure sensor 129 is configured to detect the value of the closing pressure applied on the tissues between the anvil and the cartridge when the closing mechanism performs a closing action, and transmit the value of the closing pressure to the control unit 114. The pressure sensor 129 may be arranged on the motion path of the first linear motion component, or may be arranged on the anvil 22 or the cartridge 122.

When the driving motor 120 is activated, and the firing safety switch 126 is at the closing position, the closing mechanism operates, the anvil 121 is gradually closed against the cartridge 122. When the closing main shaft 142 comes within a preset position range (often called a green zone), the closing limit switch 128 is triggered, and transmits information to the control unit 114.

Since tissues squeezed during closing have different thickness, when the closing limit switch 128 is triggered, but it does not absolutely mean the closing is adequate. Thus, the control unit 114 also receives the pressure value transmitted from the pressure sensor 129. When the pressure value also meets the preset standard, the control unit 114 may call a firing program, and transmits an instruction of controlling the driving motor 113 to drive the firing main shaft 1242. In this way, there is no excessive squeezing or inadequate squeezing, to ensure the tissue is squeezed adequately regardless of the thickness, and to ensure stable effect of the staple formation.

A closing switch 1123 and an opening switch 1124 connected to the control unit 114 are arranged outside the handle body 112. The closing switch 1123 is a common switch for closing and firing, so that the closing switch 1123 is required to be triggered no matter a closing action or a firing action is performed.

Only when the control unit 114 detects the closing switch 1123 is triggered, and the firing safety switch 126 is at the first operating position, the control unit 114 transmits an instruction of controlling the driving motor 113 to drive the closing main shaft 1232 to move. Thus, when the user operates the electric surgical stapler, the user needs to ensure the firing safety switch 126 is at the first operating position firstly, and then press the closing switch 1123 to start the closing action.

When the control unit 114 detects the closing switch 1123 is triggered, and the firing safety switch 126 is at the second operating position, the control unit 114 control the driving motor 113 to drive the firing main shaft 1242 to move.

The closing switch 1123 and the opening switch 1124 can be implemented by Hall switches.

If a button with a magnet is arranged outside the handle body 112, the control unit 114 is provided with a Hall switch. The Hall switch may be activated by the magnet. Similarly, the Hall switch may determine whether the switching between the positions of the firing safety switch 126 is detected. The Hall switch may detect the movement of the firing safety switch 126 itself, and may detect the movement of the switching driving lever 1273.

In addition, the control unit 114 can detect whether the closing switch 1123, opening switch 1124 or the firing safety switch 126 is triggered, by the arrangement of an optoelectronic switch, a micro switch or a proximity switch.

The working head 120 also includes a firing limit switch 121A configured to detect the position of the firing main shaft 1242, and transmit information of the position to the control unit 114. When the firing limit switch 121A detects the firing main shaft 1243 comes within the preset position range, the driving motor 113 stops, and the control unit 114 transmits an instruction of prohibiting the driving motor 113 to drive the closing main shaft 1232 to move. That is, when the firing is completed, the control unit 114 may block the closing switch 1123 to disable the closing switch 1123 until a new working head is replaced. The firing limit switch 121A may be an optoelectronic switch, a micro switch or a proximity switch arranged on the housing 125.

The handle 110 is removably connected to the working head 120. When the handle body 112 fits the housing 125, the handle 110 and the working head 120 are assembled together. When the housing 125 is removed from the handle body 112, the handle 110 and the working head 120 are separated from each other. The working head 120 is a circular stapling head. When the handle 110 is assembled with the working head 120, the handle 110 is a straight handle along the longitudinal direction of the working head 120, which conforms with the holding habit, to facilitate, for example, the therapy of gastrointestinal diseases.

The handle body 112 can be connected to or removed from the housing 125 rapidly. If the handle body 112 is provided with an interface part, the housing 125 is provided with a connector accordingly. During assembling, it only needs the housing 125 to be inserted into the handle body 112. The end of the output shaft 1132 is provided with an interface, and the end of the input shaft 1271 is inserted into the output shaft 1132, so the input shaft 1271 and the output shaft 1132 can assembled into a whole, while achieving the connection of the dynamical system.

A data interface 1125 connected to the control unit 114 is arranged inside the handle body 112, configured to connect the closing limit switch 128 and the pressure sensor 129. After the assembly of the handle body 112 and the housing 125, the data connector 1252 of the working head 120 is inserted into the data interface 1125.

A release button 1126 is arranged outside the handle body 112. The release button 1126 has a locking position for locking the housing and a release position for unlocking the housing. When the release button 1126 is pressed, the housing 125 is able to be inserted into the handle body 112. When the pressed release button 1126 is loosened, the housing is locked. When it is required to remove the housing 125, the release button 1126 may be pressed firstly to release locking, and then the housing 125 may be pulled out.

The housing 125 is also provided with a window to view the motion position of the closing main shaft 1232, to facilitate the user to turn the adjustment knob manually in accordance with specific conditions. The adjustment knob 115 is able to supply a manual mode, to deal with the condition of getting stuck. In addition, when the thickness of the tissue exceeds the maximum closing ability of the device, the manual mode may be activated to make the driving motor 113 get away from the overload endless loop. In the manual mode, the anvil 121 and the cartridge 122 may be opened, or continue to finish the firing.

The electric surgical stapler further includes a replaceable battery pack 117 connected to the handle body 112, and configured to supply power to the driving motor 113. The handle body 112 is provided with an indicator light (not shown) connected to the control unit 114. The indicator light may show the closing state, the firing state or the battery level of the battery pack.

The electric surgical stapler according to the present disclosure can detect the closing pressure and the closing stroke simultaneously, to ensure the tissue is squeezed adequately regardless of the thickness of the tissue, to ensure a stable effect of the staple formation.

In the electric surgical stapler according to the present disclosure, the working head is a single-use component. The handle 110 removeably fits the working head 120. When replacing, only the working head 120 is required to be replaced, while the handle 110 can be used repeatedly after disinfection, to reduce cost. But it is necessary to point out that the above conception of detecting both the closing pressure and the closing stroke is also applicable for an integrated stapler.

The above working head 120 is a circular stapling head, but can be other types of working heads, for example, a linear stapling head.

Figure 4:
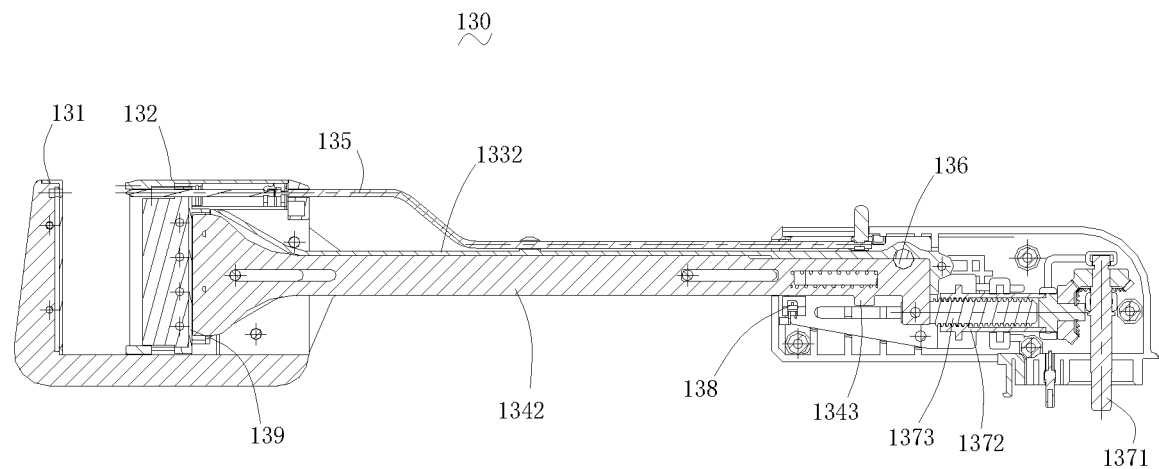
FIG. 4 is a schematic diagram illustrating a cross section of a linear stapling head.

With reference to FIG. 4, a linear working head 130 is provided, which is provided with both a closing limit switch and a pressure sensor to detect whether both the closing stroke and closing pressure meet requirements. The working head 120 can be replaced with the linear working head 130. The linear working head 130 fits the handle 110, and the mechanical connection form is the same as the above embodiment, with a difference that the device is in a shape of a gun after assembling.

With reference to FIG. 4, the linear working head 130 includes an anvil 131, a cartridge 132, a closing mechanism, a firing mechanism, and a housing 135 housing the closing mechanism and the firing mechanism.

The closing mechanism includes a closing lever 1332. The firing mechanism includes a firing lever 1342. The closing lever 1332 and the firing lever 1342 can move in a straight line together, or move in a straight line relative to one another.

A limit rotation shaft 136 is arranged outside the housing 135. The limit rotation shaft 136 can limit both the closing lever 1332 and the firing lever 1342 in the axial direction, to allow the closing lever 1332 and the firing lever 1342 to move together. When the limit rotation shaft 136 rotates so that the limit rotation shaft 136 is separated from the firing lever 1342 in the axial direction, the firing lever 1342 can move in a straight line relative to the closing lever 1332.

A transmission mechanism is arranged outside the housing 135, including a input shaft 1371, a thread bushing 1372 that is rotatable when driven by tapered teeth, and a screw 1373 in a threaded connection with the thread bushing 1372, and the rotation of the screw 1373 is limited so that the screw 1373 only makes axial movement. A flat fitting portion may be arranged between the screw 1373 and the thread bushing 1372, so that the screw 1373 may only translate in the axial direction. The screw 1373 is connected to the firing lever 1342 to drive the firing lever 1342 to move in a straight line. The limit rotation shaft 136 is equivalent to a firing safety switch which must be operated to switch the closing lever 1332 and the firing lever 1342.

A closing limit switch 138 is arranged inside the housing 135. At closing, the firing lever 1342 may drive the closing lever 1332 to move together, and when firing lever 1342 moves to a specified position, the raised portion 1343 on the firing lever 1342 trigger the closing limit switch 138. At firing, the limit rotation shaft 136 is operated to separate the closing lever 1332 from the firing lever 134, the firing lever 134 does not drive the closing lever 1332 when moving, and the raised portion 1343 moves and triggers the closing limit switch 138 again, to finish the firing of the cartridge.

The pressure sensor 139 is arranged on the cartridge 132. Specifically, the pressure sensor 139 may be arranged between the staple ejecting assembly of the anvil 132 and the firing lever 1342. During closing, the firing lever 1342 drives the closing lever 1332 to push the staple ejecting assembly to drive the cartridge 132 to move forward. Thus the pressure sensor 139 can acquire the closing pressure, can transmit the closing pressure to the control unit 114. During firing, in addition to the staple ejecting assembly, the cartridge 132 is limited in the axial direction, and the firing lever 1342 continues to push the staple ejecting assembly, so that the staple ejecting assembly moves forward relative to the cartridge 132 to finish the firing. Alternatively, the pressure sensor 139 may be arranged on the motion path of the closing lever 1332.

The linear working head 130 fits the handle 110, and is able to detect both the closing pressure and the closing stroke, to ensure the tissue is squeezed adequately regardless of the thickness, and to ensure stable effect of the staple formation.

Whether the electric surgical stapler is comfortable for use and has abilities of precise closing, staple formation and cutting depends on good communication between the handle 110 and the working head 120 (or 130). For this reason, the present disclosure provides a method for controlling closing and firing of the above circular surgical stapler or linear surgical stapler.

Figure 5:
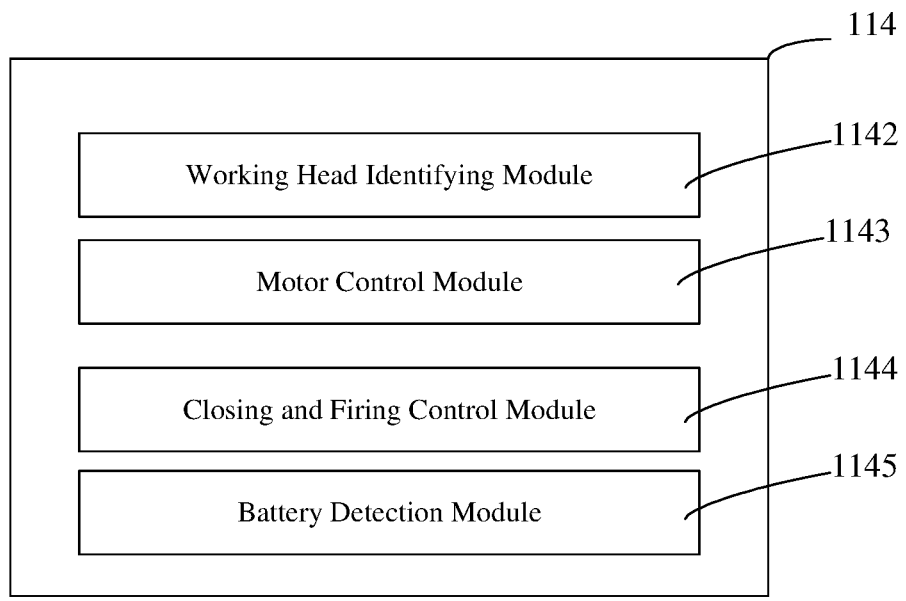
FIG. 5 is a module diagram of an control unit.
Figure 6:
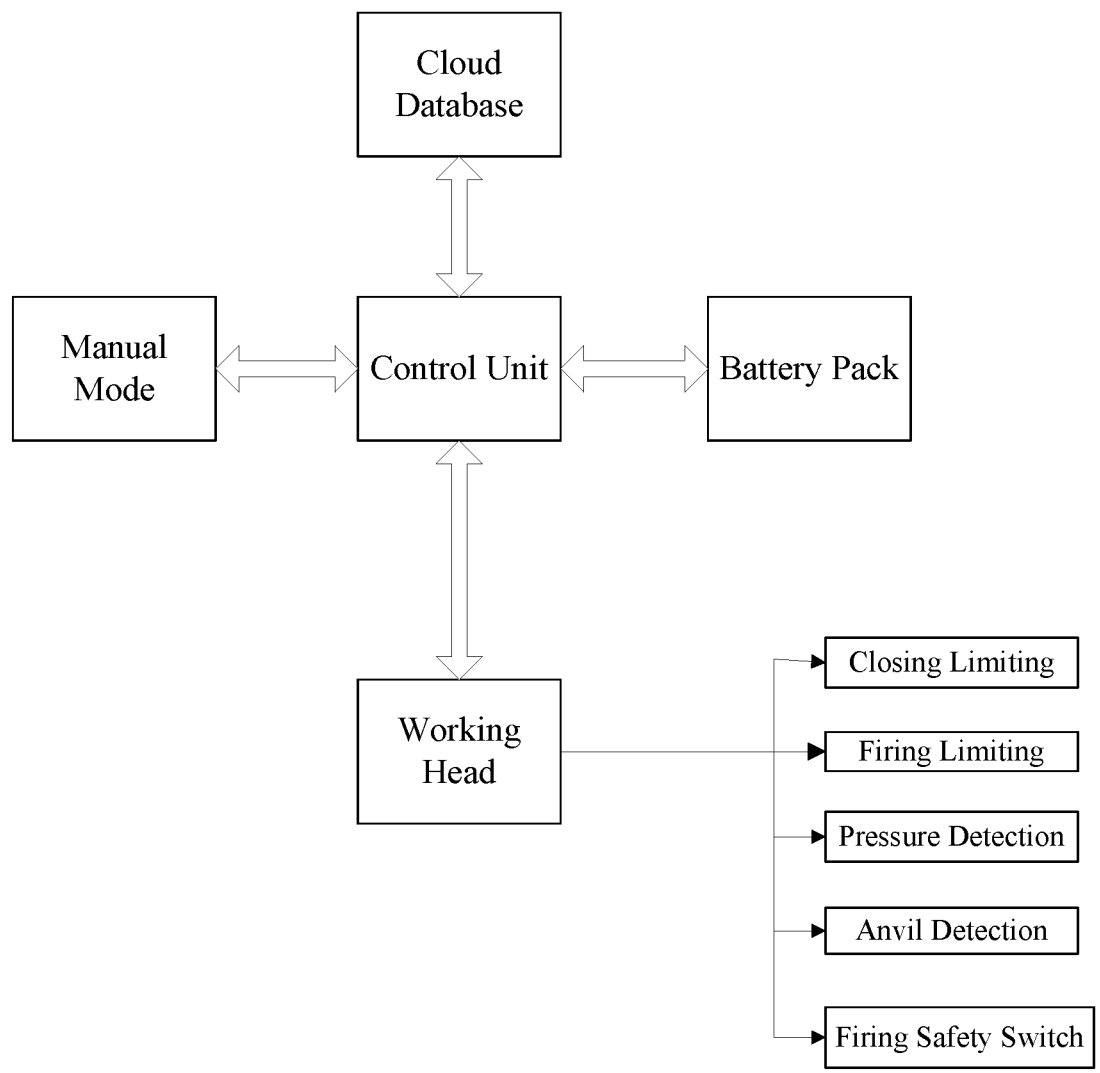
FIG. 6 is a schematic diagram illustrating a method for controlling closing and firing of the electric surgical stapler.

With reference to FIG. 5, the control unit 114 includes: a working head identifying module 1142, configured to acquire identification information of the working head; a motor control module 1143, configured to control starting and stopping of the driving motor 113; a closing and firing control module 1144, configured to receive information from the closing limit switch 138 and the firing safety switch 139; and a battery detection module 1145, configured to detect information of the battery pack. With reference to FIG. 6, during the closing and firing, performance of both the closing and firing actions needs the control unit 114 to communicate with the working head 120 (130), and transmit control instructions based on the feedback. The data record by the control unit 114 can be transmitted to a cloud database. The control unit 114 can communicate with the cloud database through Bluetooth or other wireless transmission modes, to download or unload system data, which facilitates the manufacturer to update the control program remotely. The control unit 114 may record the usage during surgery and feed back to the cloud database, which facilitates the improvement of the products. The relevant steps are described in detail below.

1. When the battery pack 117 is connected to the handle 110, the control unit 114 may read the battery information, for example, manufacturer, battery level and over-current, in the battery pack 117 through the battery detection module 1145. Different standards may be set according to needs. If the battery level is below a specified security value, for example, 60%, the power indicator light on the handle may flash to prompt to change the battery, and it means the battery cannot meet the requirement of this surgery. If the power indicator light flashes during surgery, it prompts to change the battery. When a battery supply is normally connected, the closing switch 1123 may be pressed to verify whether the handle 110 is operating. The communication between the control unit 114 and the battery may be identified by different resistance values. If there is no communication between the control unit 114 and the battery, the device is unable to be used, to prevent electricity shortages caused by a non-verified battery during surgery. It should be noted that the battery level may be detected repeatedly for several times or in real time, to ensure there is enough power.

2. The identification information of the working head may be acquired. When the working head is connected, the control unit 114 begins to verify the identity of the working head, that is, the validity of the working head and the type of the working head, specifically. When the working head 120 (or 130) is connected, the handle 110 may perform two steps to verify the identification of the working head. Firstly, a temperature sensor chip may be used to identify the unique identification of the original manufacturers working head to avoid unknown impact of unknown working heads on the surgery. The identification may also be determined by Bluetooth/NFC/IC pairing. Secondly, the type of the working head (including circular stapler, linear stapler, and straight linear cutter may be identified. If the definition of these three types of working heads is preset in advance, the type of the connected working head may be determined by a linear switch or voltage variation caused by being connected to a resistor of a different resistance, or may be determined by different kinds of connecting methods of pins on the USB or other connectors. When the working head is identified normally, the indicator light may transform from flashing into keeping on. If the connection is abnormal, all of the three indicator lights may flash, or one or two of the three indicator lights may flash. Other similar ways are possible.

3. The working head may be controlled to be reset automatically. In this step, the state information of the firing safety switch on whether the firing safety switch is at the closing position or the firing position may be acquired. Only when the firing safety switch is at the closing position and the closing limit switch is triggered, the anvil and the cartridge of the working head may be controlled to open a corresponding distance from a closing state, based on the identification information of the working head.

The working head may be reset automatically after normal connection, that is, the anvil and the cartridge open a certain distance so that the tissue to be squeezed is able to enter a space between the anvil and the cartridge. The working head being reset automatically has two preconditions. One is that: the firing safety switch is triggered and the firing safety switch is not at the firing position. The other is that: closing limit switch (often called a green zone limit switch) is triggered. For example, if the firing safety switch is a Hall switch, the control unit 114 may determine the firing safety switch is not at the firing position when the Hall switch is triggered to produce a signal of low level.

The above preconditions may ensure the detection of functions of the firing safety switch and the closing limit switch when the handle communicates with the working head initially, to guarantee the successful implement of the subsequent surgery, to avoid surgery accidents. If there is a mistake found, the working head may be replaced immediately at this time.

The distance to be opened at the automatic reset is different as the type of the working head. In general, if a circular stapler is identified, the working head may be reset automatically, and the anvil and the cartridge may open a distance of about 51 mm. If a linear stapler is identified, the working head may be reset automatically, and the anvil and the cartridge may open a distance of about 17 mm. If a straight linear cutter stapler is identified, the working head may be reset automatically, and the anvil and the cartridge may open a distance of about 20 mm 4. The closing action may be performed. Whether the closing switch is triggered and the firing safety switch is at the closing position may be detected, if so, start the driving motor and control operation of the closing mechanism to gradually close the anvil and the cartridge, and stop the driving motor when the closing limit switch is triggered, otherwise switch the firing safety switch to the closing position, and continue to detect whether the closing switch is triggered.

Take the circular stapling head (working head 120) as an example. The activation of the closing mechanism 123 has two preconditions. One is that the firing safety switch 126 is at the closing position, and the other is that the closing switch 1123 is pressed. Only when the two preconditions are both met, the motor control module 1143 can activate the driving motor 113 to operate, which allows the closing mechanism 123 to operate in turn. When the closing mechanism 123 moves to a preset position, the closing limit switch 128 is triggered. When the driving motor 113 stops operating, an indicator light may be used to prompt that the closing is adequate, for example the indicator light may transform from not lighting into flashing. It is similar for the linear stapler and the straight linear cutter stapler that when the closing is adequate, the closing limit switch is triggered, and the driving motor 113 stops operating.

When the closing is adequate, the closing switch 1123 is blocked by the control unit 114, and in a disabled mode, to prevent the tissue from being squeezed exceedingly. The adjustment knob 115 may be turned on to adjust the closing mechanism 123 finely so that the thickness of the tissue meets the requirement. In this step, when the firing safety switch 126 is not triggered (at a firing position), the closing switch 1123 is at a disabled mode, and the firing safety switch 126 is required to be switched to the closing position for normal closing, to prevent fault firing when the closing is adequate.

During the closing, the driving motor 113 stops operating when the closing switch 1123 is loosened. After the closing, the firing safety switch 126 is switched to the firing position, and the firing is waited. At this time, the opening switch 1124 is blocked to be in the disabled mode. If the firing safety switch is switched to the closing position, the opening switch 1124 can operate and open the jaw for clamping the tissue again, and the closing switch 1123 is blocked to be in the disabled mode. The closing limit switch 128 may be designed to have an adjustable position to fit tissues of different thicknesses, and the position of the closing limit switch may be set before the closing according to the thickness of the tissue.

5. The firing action may be performed. Whether the closing switch is triggered and the firing safety switch is at the firing position may be detected, and if so, activate the driving motor to drive the firing mechanism to operate, otherwise, switch the firing safety switch to the firing position, and continue to detect whether the closing switch is triggered.

The preferment of the firing action should meet three preconditions: the firing safety switch 126 is at the firing position; the closing switch 1123 is triggered; and the closing limit switch is triggered. Only when the three preconditions are met, the closing and firing control module 1144 allows the motor control module 1143 to activate the driving motor 113 to make the firing mechanism 124 operate.

When the firing mechanism 124 triggers the firing limit switch 121A, the firing is completed, which may be prompted by an indicator light. Then the driving motor 113 rotates in reverse to complete firing reset automatically. In addition, the driving motor 113 may rotates in reverse when a predetermined rotation rate or a predetermined time is reached, to reset the firing mechanism 124. At this time, the closing switch 1123 is blocked by the control unit 114 to be in the disabled mode.

The firing procedure of the linear stapler assembled by the linear working head 130 and the handle 110 is similar to the circular stapler assembled by the working head 120 and the handle 110.

For the straight linear cutter stapler, it may be set to reset automatically in one second when the closing switch is loosened, to meet requirements on tissues of different lengths. If the closing switch is held down, the driving motor stops operating when the firing limit switch is triggered. The driving motor may be reset for example, in two seconds when the closing switch is loosened.

For the control method according to the present disclosure, the handle 110 is kept in communication with the working head 120 (or 130) during the processes of mounting the working head 120 (or 130) into the handle 110, closing and firing, to ensure that the next action is performed only when the feedback meets expectations, to avoid fault operations. In addition, the closing limit switch and the pressure sensor can ensure a good squeezing effect to guarantee the effect of staple formation.

The present invention may be carried out in other specific ways than those herein set forth without departing from the scope and essential characteristics of the invention. The present embodiments are, therefore, to be considered in all respects as illustrative and not restrictive.

While embodiments and applications have been shown and described, it would be apparent to those skilled in the art having the benefit of this disclosure that many more modifications than mentioned above are possible without departing from the inventive concepts disclosed herein. The invention, therefore, is not to be restricted except in the spirit of the appended claims.

What is claimed is:

1. An electric surgical stapler is provided, comprising:

a driving motor, having an output shaft;

a working head, including an anvil, a cartridge, a closing mechanism, a firing mechanism, a closing limit switch, and a firing safety switch, wherein the closing limit switch is configured to detect whether a closing stroke of the closing mechanism comes within a predetermined range, the firing safety switch has a closing position and a firing position, the firing safety switch is configured to allow the output shaft to transmit power to the closing mechanism at the closing position, and to allow the output shaft to transmit power to the firing mechanism at the firing position; and a control unit, including:

a working head identifying module, configured to acquire identification information of the working head;

a motor control module, configured to control starting and stopping of the driving motor;

a closing and firing control module, configured to receive closing stroke information transmitted from the closing limit switch, and receive position information transmitted from the firing safety switch;

a closing switch, configured to transmit a closing instruction to the motor control module; and an opening switch, configured to transmit an opening instruction to the motor control module.

2. The electric surgical stapler of claim 1, further comprising:

an adjustment screw for controlling rotation of the output shaft, configured to adjust the output shaft manually to control the closing mechanism or firing mechanism.

3. The electric surgical stapler of claim 1, further comprising:

a pressure sensor, configured to detect a closing pressure value of the anvil and the cartridge during a closing process, and transmit the closing pressure value to the control unit.

4. The electric surgical stapler of claim 1, further comprising:
a firing limit switch, configured to detect whether a firing stroke of the firing mechanism comes within a predetermined range, and transmit a detection result to the control unit.

5. A method for controlling closing and firing of the electric surgical stapler of claim 1, comprising:
acquiring the identification information of the working head;
acquiring state information of the firing safety switch at the closing position or firing position, and controlling the anvil and the cartridge of the working head to open for a corresponding distance from a closing state, based on the identification information of the working head, when detecting the firing safety switch is at the closing position and the closing limit switch is triggered;
detecting whether the closing switch is triggered and the firing safety switch is at the closing position; if it is, starting the driving motor and controlling operation of the closing mechanism to gradually close the anvil and the cartridge, and stopping the driving motor when the closing limit switch is triggered, otherwise, switching the firing safety switch to the closing position, and continuing to detect whether the closing switch is triggered; and
detecting whether the closing switch is triggered, the firing safety switch is at the firing position, and the closing limit switch is at a triggering position, and if it is, activating the driving motor to drive the firing mechanism to operate, otherwise, switching the firing safety switch to the firing position, and continuing to detect whether the closing switch is triggered.

6. The method of claim 5, further comprising:
adjusting the closing mechanism manually when the closing limit switch is triggered and the driving motor is stopped, and switching the firing safety switch from the closing position to the firing position after the manual adjustment.

7. The method of claim 5, wherein the electric surgical stapler further comprises a pressure sensor configured to detect the closing pressure value of the anvil and the cartridge during a closing process, and transmit the closing pressure value to the control unit; and the control unit is configured to transmit an instruction of controlling the driving motor to drive movement of the firing mechanism, when the closing limit switch is triggered and the pressure value transmitted by the pressure sensor meets a preset standard.

8. The method of claim 5, wherein the electric surgical stapler further comprises a firing limit switch configured to detect whether a firing stroke of the firing mechanism comes within a predetermined range, and the driving motor is adapted to stop when the firing limit switch is triggered.

9. The method of claim 8, further comprising:
switching the firing safety switch to the closing position and making the driving motor rotate inversely to reset the closing mechanism, when the firing limit switch is triggered and the driving motor is stopped.

10. The method of claim 5, wherein the acquiring the identification information of the working head includes:
verifying the validity of the identification of the working head; and
identify a type of the working head.

* * * * *